(12) United States Patent
Meinel et al.

(10) Patent No.: US 8,452,613 B2
(45) Date of Patent: May 28, 2013

(54) MULTIPLE MODALITY COMPUTER AIDED DIAGNOSTIC SYSTEM AND METHOD

(75) Inventors: Lina Arbash Meinel, Homewood, IL (US); Gillian Maclain Newstead, Chicago, IL (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 46 days.

(21) Appl. No.: 12/996,031

(22) PCT Filed: Jun. 1, 2009

(86) PCT No.: PCT/IB2009/052296
§ 371 (c)(1),
(2), (4) Date: Dec. 3, 2010

(87) PCT Pub. No.: WO2009/150566
PCT Pub. Date: Dec. 17, 2009

(65) Prior Publication Data
US 2011/0087089 A1    Apr. 14, 2011

Related U.S. Application Data

(60) Provisional application No. 61/060,510, filed on Jun. 11, 2008.

(51) Int. Cl.
*G06Q 10/00* (2012.01)
(52) U.S. Cl.
USPC .................. 705/2; 705/3; 600/407; 600/409; 600/437
(58) Field of Classification Search
USPC 600/407–419, 437–463; 705/2; 382/128–132
See application file for complete search history.

(56) References Cited

U.S. PATENT DOCUMENTS

| | | | |
|---|---|---|---|
| 6,734,880 B2 * | 5/2004 | Chang et al. | 715/738 |
| 7,103,205 B2 * | 9/2006 | Wang et al. | 382/132 |
| 7,313,260 B2 * | 12/2007 | Wang et al. | 382/128 |
| 7,597,663 B2 * | 10/2009 | Wang et al. | 600/437 |
| 7,738,683 B2 * | 6/2010 | Cahill et al. | 382/128 |
| 2003/0212327 A1 * | 11/2003 | Wang et al. | 600/437 |
| 2005/0089205 A1 | 4/2005 | Kapur et al. | |
| 2006/0010013 A1 * | 1/2006 | Yamatake | 705/2 |
| 2007/0036402 A1 * | 2/2007 | Cahill et al. | 382/128 |
| 2009/0003732 A1 * | 1/2009 | Oda | 382/305 |
| 2009/0171244 A1 * | 7/2009 | Ning et al. | 600/567 |
| 2009/0297441 A1 * | 12/2009 | Canham et al. | 424/1.61 |
| 2009/0312601 A1 * | 12/2009 | Shigemori | 600/103 |
| 2009/0312640 A1 * | 12/2009 | Wang et al. | 600/443 |
| 2010/0088113 A1 * | 4/2010 | Kubota | 705/2 |

FOREIGN PATENT DOCUMENTS
WO  2005117711 A2  12/2005

OTHER PUBLICATIONS

Giger, M. L.; Computerized Analysis of Images in the Detection and Diagnosis of Breast Cancer; 2004; Seminars in Ultrasound, CT and MR; Grune and Stratton, Orlando, FL; 25(5)411-418.

* cited by examiner

*Primary Examiner* — Sanjay Cattungal

(57) ABSTRACT

A diagnostic system having an image loader including a processor for processing multiple modality images, at least one of the multiple modality images being a mammogram image, the processing including generating diagnostic information based on a computer aided diagnostic tool and an image viewer simultaneously displaying the multiple modality images.

17 Claims, 3 Drawing Sheets

MULTIPLE MODALITY COMPUTER AIDED DIAGNOSTIC SYSTEM AND METHOD

CROSS REFERENCE TO RELATED APPLICATIONS

This application claims the benefit of U.S. provisional application Ser. No. 61/060,510 filed Jun. 11, 2008, which is incorporated herein by reference.

BACKGROUND

Mammography is currently the method of choice for screening for breast cancer. However, other breast imaging exams are often used to supplement the mammogram when further evaluation is necessary. For example, an ultrasound is typically used for further evaluation of lesions found on a mammography or palpable lesions not seen on mammograms. Ultrasounds are also used to image the dense breasts of young women (i.e., 30-50 years of age) and especially for cyst and fibroderma cases which are usually hard to find by palpation or by other imaging modalities. Magnetic resonance images (MRIs) can be useful for further evaluation of questionable findings, as MRIs have superior detection sensitivity due to topographic properties, larger field of view and greater soft tissue contact. Research has shown that 10-30% of lesions missed by mammography are visible in an MRI.

To include all of the advantages of the various modalities, physicians currently read MRIs accompanied with mammograms and/or ultrasounds. This is a time consuming and difficult process. Moreover, breast lesions in the MRIs, mammograms and/or ultrasounds need to be detected and classified in an expeditious and accurate manner.

SUMMARY OF THE INVENTION

The exemplary embodiments described herein include a system having an image loader including a processor for processing multiple modality images, at least one of the multiple modality images being a mammogram image, the processing including generating diagnostic information based on a computer aided diagnostic tool and an image viewer simultaneously displaying the multiple modality images.

DETAILED DESCRIPTION

The following exemplary embodiments are related to a computer aided diagnostic (CAD) system for simultaneously analyzing images of multiple modalities. It should be noted, however, that although the exemplary embodiments are described in regard to image modalities used for diagnosing breast cancer, other diseases or illnesses may be similarly diagnosed.

Figure 1:
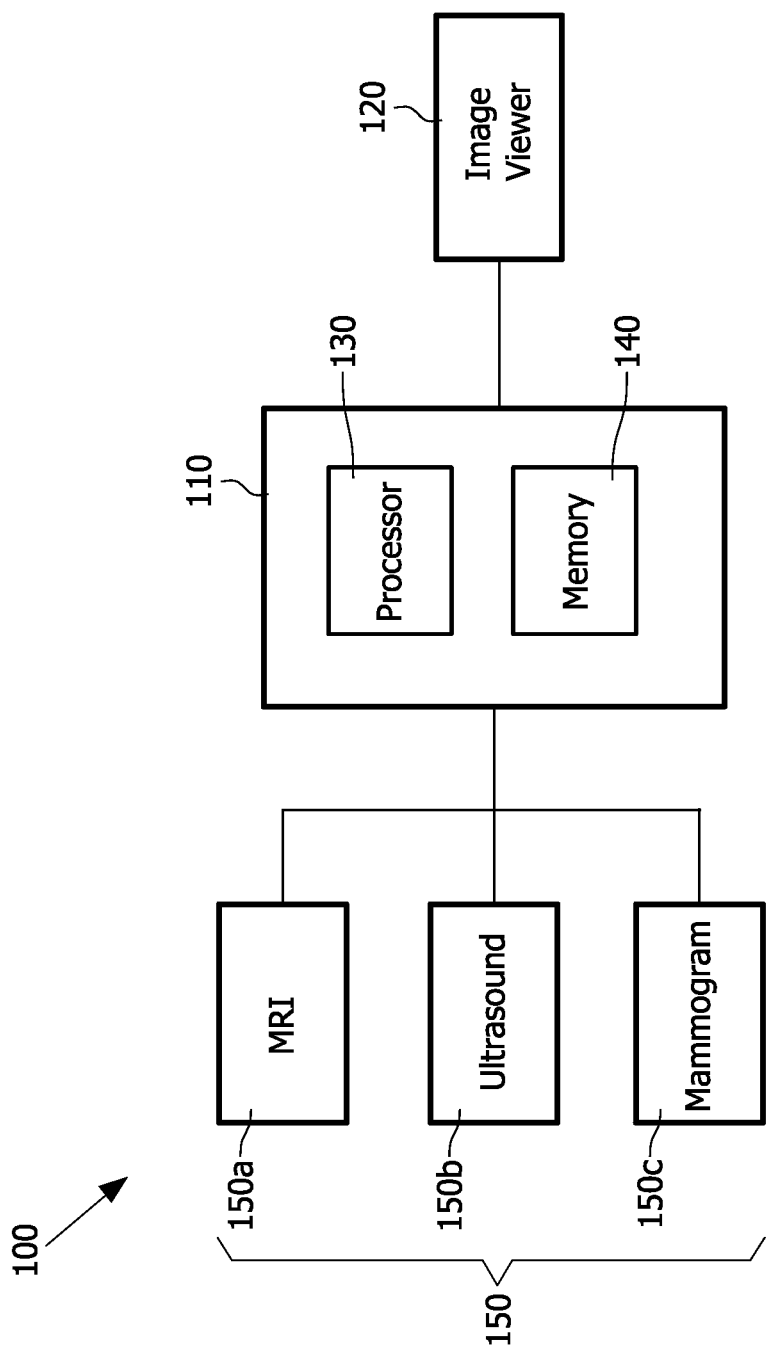
FIG. 1 shows a schematic diagram of a system according to an exemplary embodiment.

FIG. 1 shows a schematic diagram of a system 100 according to an exemplary embodiment. The system 100 is, for example, a CAD system for diagnosing breast cancer. The system 100 comprises an image loader 110 and an image viewer 120. The image loader 110 is used to load images 150 acquired from multiple medical imaging modalities to be processed and displayed on the image viewer 120. The multiple modality images 150 include, for example, an MRI image 150a, an ultrasound image 150b and a mammogram image 150c. It will be understood by those having skill in the art, however, that other types of modality images, or an additional number of modality images, may also be processed and displayed and that system 100 may be adapted for the detection of other illnesses or diseases, which may require modality images other than an MRI image 150a, an ultrasound image 150b or a mammogram image 150c. For example, a CT image for monitoring the spread of cancer and/or a non-mammogram x-ray image may be alternatively added to or may replace one or more of the images.

The image loader 110 includes a processor 130 and/or a memory 140. The processor 130 processes the multiple modality images 150 to be displayed on the image viewer 120. The multiple modality images 150 are either temporarily or permanently stored in the memory 140. The image loader 110 is capable of receiving and processing the multiple modality images 150 from one or more image scanners to which the image loader 110 is connected. Thus, the image loader 110 is, for example, connected to an MRI scanner for receiving and processing an MRI image 150a, an ultrasound scanner for receiving and processing an ultrasound image 150b, and an X-ray scanner for receiving and processing a mammogram image 150c. Those of skill in the art will understand that the image loader 110 may be additionally or alternatively connected to a CT scanner or other modality type scanner depending on the circumstances.

Additionally, the processed multiple modality images 150 may be stored in the memory 140 for future retrieval(s) and processing instead of instant processing. Thus, in use or as a practical matter, the image loader 110 does not need to be connected to any image scanners because memory 140 is capable of storing previously scanned multiple modality images 150, which can be processed later. Thus, the processor 130 of the image loader may process the stored multiple modality images 150 such that the images 150 may be simultaneously displayed on the image viewer 120.

Alternatively, the image loader 110 may be connected to at least one image scanner such that any image of a modality that has not been directly scanned and received by the image loader 110 may be later acquired and stored in a memory 140 of the image loader 100. For example, the system 100 may be connected to an MRI scanner which generates MRI image 150a that is received by the image loader 110. The ultrasound and mammogram images 150b and 150c, or alternative modality images such as CT images, may be stored on the memory 140 already. The image loader 110 may process the multiple modality images 150 from the various sources (i.e., memory 140, an MRI scanner) for display on the image viewer 120.

Those skilled in the art will understand that the images may be stored in memory 140 in any number of ways, such as, for example, by connection to a network location from which the images may be downloaded, by connection to a flash memory card, or by connection to a Picture Archiving and Communication System (PACS).

The image viewer 120 is, for example, a CRT display device, LCD display device, plasma display device or any other display means capable of displaying the multiple modality images 150. It will be understood by those having skill in the art that the image viewer 120 may also be a 5MP monitor for mammogram display in compliance with FDA requirements for diagnosing mammograms.

Figure 2:
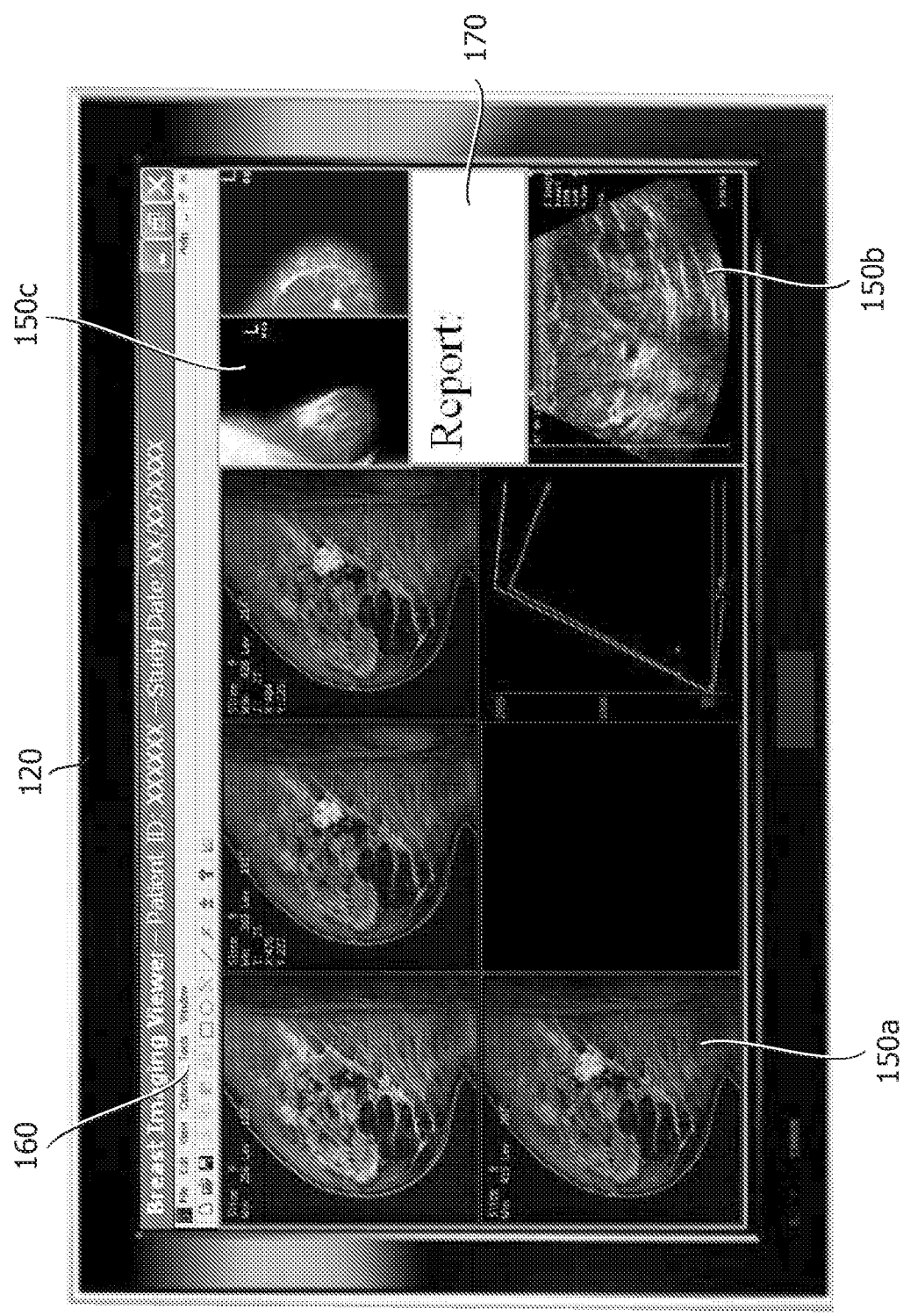
FIG. 2 shows an exemplary display screen that may be used with the system of FIG. 1.

FIG. 2 shows an exemplary embodiment of an image viewer 120 displaying a toolbar 160 along with MRI image(s) 150a, an ultrasound image 150b, a mammogram image 150c and a report 170 including patient information and a follow up report. The toolbar 160 includes menus and/or icons for the various system capabilities. The MRI images include all image sequences such as, for example, pre and post contrast, T1 and T2 weighted image and other reconstructed images, maximum intensity projection (MIP) and multi-planar reconstruction (MPR) in different views [coronal, axial, and sagittal] and time/intensity curves). The mammogram images include, for example, a medio-lateral (ML) view and a cranocaudal (CC) view. The ultrasound images include, for example, real-time video and/or digital images in 2D, 3D or multiple dimensions. The multiple modality images 150 are displayed simultaneously so that the images 150 may be directly compared across modalities.

The image loader 110 and the image viewer 120 may be embodied as a single workstation comprising a computing system and monitor such that the multiple modality images 150 may be processed by the processor 130 of the computing system and displayed on the computer monitor. However, it will be understood by those in the art that any processing and displaying means may be used within the spirit of this disclosure.

The toolbar 160, which is displayed on image viewer 120, includes menus and icons for various tool functions to be processed by the processor 130. A physician interacts with the toolbar 160 by, for example, touching the image viewer 120 where the image viewer 120 is a touch sensitive screen or using one or more input devices such as a mouse and/or keyboard that is connected to the image viewer 120 or image loader 110. The system 100 may include window/level control and region of interest tools. These tools are used by a physician (e.g., radiologist) to mark suspicious lesions that are visible in any of the multiple modality images 150. After the regions of interest have been marked, they are saved to a file for subsequent review and analysis. The file may be stored in the memory 140. The control tools may also include functions to allow saved images to be loaded from the memory 140. Other control tools may include saving, opening, changing views, zooming, etc. It will be understood by those in the art that other window/level control tools may also be included.

The toolbar 160 may also include other image analysis tools such as, for example, image subtraction, image segmentation, and other advanced functions for analyzing pre-selected lesions. Image subtraction is used by physicians to view differences between images, which may be a post-contrast image minus a pre-contrast image, to increase the conspicuity of enhancing lesions. This may be especially helpful when the lesion or lesion background exhibits a high signal prior to contrast administration. Image subtraction is also useful for physicians to assess the enhancement kinetics of a suspicious lesion on an MRI, often called the time-intensity curve. Such curves are generated from a series of post-contrast images captured at different times. The curves may also be displayed on the image viewer 120.

Tools for image segmentation, such as adaptive thresholding, fixed thresholding, and/or grayscale morphology may be used interactively to identify lesions of interest. Other segmentation tools that may also aid in identifying a region of interest include region growing, active contour, ellipse fitting, etc. The image segmentation tools may also include segmentation enhancement tools such as blood vessel rejection tools. These advanced function tools are used for analyzing pre-selected lesions. The advanced function tools may include extraction tools which may extract features (e.g., shape, texture) from the selected lesions and clarify lesions of interest as benign or malignant using a database of previously diagnosed cases, which may be stored in the memory 140 of the system 100. The advanced function tool may also generate a confidence percentage associated with the assessment and a follow up report, which may be displayed in the report section 170 on the image viewer 120.

In addition to the function tools described above, the system 100 may be capable of recognizing regions of interest that are not visible to the physician or those that have been overlooked by the physician. These lesions may be marked on the images 150 for further analysis by a physician using the tools of the toolbar 160.

Figure 3:
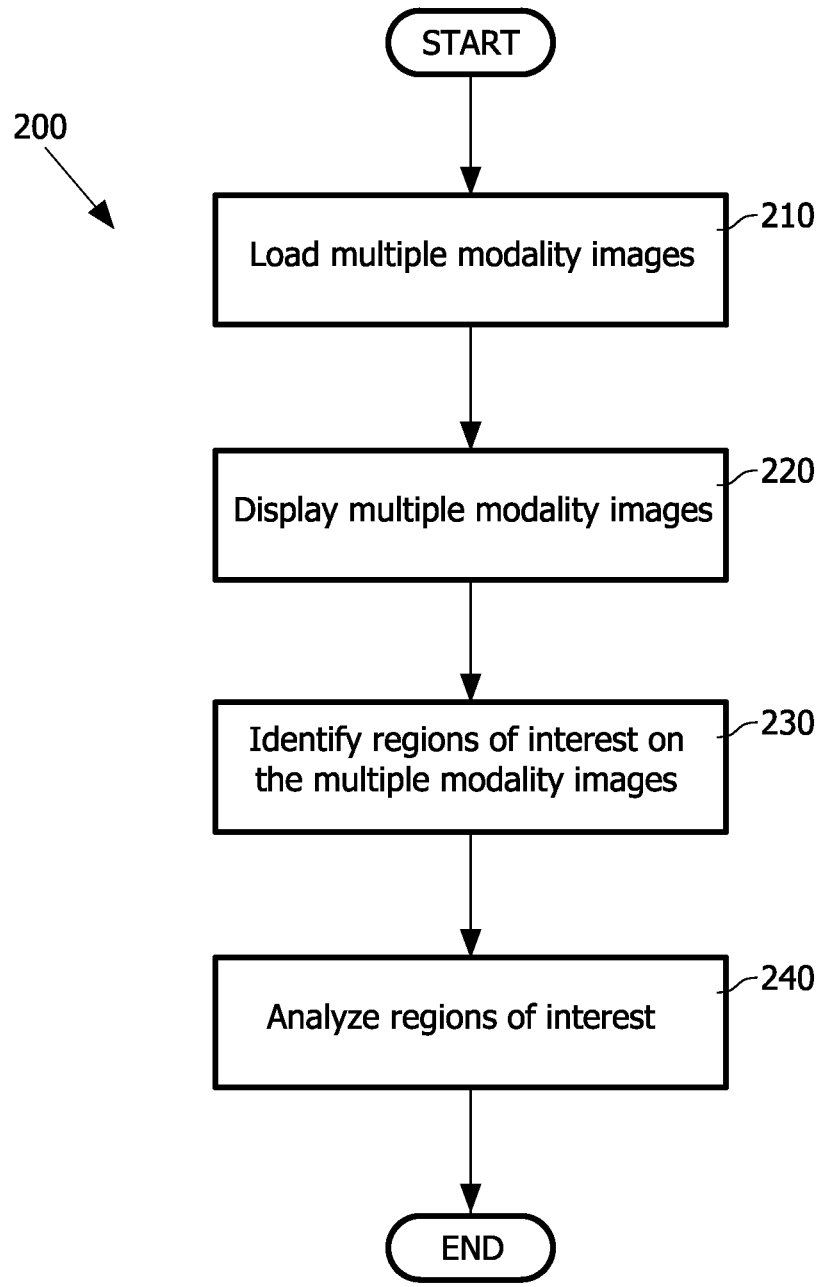
FIG. 3 shows a flow diagram of a method according to an exemplary embodiment.

An exemplary method 200 of the present invention is shown in FIG. 3, in which the multiple modality images 150 are loaded via the image loader 110 in step 210 and displayed on the image viewer 120 in step 220. Subsequently, regions of interest may be identified in step 230 and these regions of interest analyzed in step 240. The multiple modality images 150 may be loaded in a variety of ways. Loading the multiple modality images 150 may require that the image loader 110 be connected to one or some combination of image scanners (i.e., MRI scanner, ultrasound scanner, X-ray scanner for mammograms) so that one or more of the multiple modality images 150 can be scanned and digitized by the image scanner, and received by the image loader 110 for processing. Alternatively, the multiple modality images 150 are loaded from a memory 140 of the image loader 110 in which the various multiple modality images 150 may have been previously stored. Multiple modality images 150 may also be loaded from any combination of modality scanning to the image loader 110 and retrieval of previously stored images from memory 140 of the image loader 110.

In step 220, the image viewer displays the multiple modality images 150, along with the toolbar 160 and the report 170. The display of the image viewer 120 may be divided into separate sections such that the toolbar 160, the report 170 and images 150 of each modality are displayed in a separate section. For example, if the modalities are an MRI, an ultrasound, and a mammogram, the three most commonly used image modalities for diagnosing breast cancer, then each modality is displayed in a separate section on the image viewer 120. FIG. 2 shows for example, MRI image(s) 150a displayed in a first section, ultrasound images 150b displayed in a second section, and mammogram images 150c displayed in a third section.

MRI images may include pre and post-contrast images, T1 and T2 weighted images. It will be understood by those in the art that contrast agents may be used in MRIs to delineate areas of interest. It will also be understood by those in the art that T1 and T2 weighted images may be used to generate time/intensity curves. These curves may also be displayed in the first section. The first section may also include additional space for other MRI images or graphs that may aid in diagnosis such as reconstructed images (e.g., subtracted images, MIP and MPR in different views [coronal, axial, and sagittal] and time/intensity curves). The ultrasound image 150b of the second section may be a still image or a video loop of the ultrasound.

Mammogram images 150c of the third section may include the ML and CC views of the breast, the two main views of the breast when detecting lesions in the breast. In cases where additional views are necessary (e.g., magnified mammography view and previous mammography study), these images may also be displayed in the third section. The third section may also include additional space for any other necessary images or information.

The toolbar 160 and the report 170 are also displayed in their own sections in step 220. The toolbar 160 section includes menu options and icons for various tool functions. The report 170 section displays patient information (e.g., age, gender, medical history) as well as any reports generated by the system 100. The report 170 may also include additional space for including any physician comments regarding the images, or possible diagnoses that may be referred to at a later time. It will be understood by those in the art that the display of the image viewer 120 may include any number of sections to accommodate the number of image modalities being analyzed.

Regions of interest may be identified, in step 230, in a number of different ways. The regions of interest may be identified by the physician upon inspection of the simultaneously displayed multiple modality images 150 or by the system 100, which may identify possible lesions based on previously identified lesions. The regions of interest may then be marked on the images 150. The marked multiple modality images 150 may be stored in the memory 140 such that they may be subsequently reviewed and/or analyzed by the physician. Analysis tools from the toolbar 160 may also be used to aid the physician in marking regions of interest.

Once regions of interest are identified, the marked areas of the images may be analyzed in step 240 using the available tool functions displayed in the toolbar 160. The physician may select a variety of analysis tools from the toolbar 160 such as image segmentation, image subtraction, feature extraction, etc. Using the analysis tools, the physician may be able to determine whether the lesions identified in step 230 are lesions of concern, and whether they are benign or malignant. If an analysis tool such as feature extraction is used, the system 100 may be able to use the feature extraction values to assess whether the identified regions of interest are cause for concern, and provide a confidence percentage along with a follow up report, which may be displayed in the report section 170 on the image viewer 120. In a further embodiment, in addition to selecting tools from the toolbar 160, a physician may select analysis tools by pressing hot-keys on an input device, which may be connected to the image loader 110. These hot-keys may be pre-set or set by the physician.

Thus, by simultaneously displaying the multiple modality images 150 and by providing analysis tools, the system and method described herein will allow physicians to identify and analyze regions of interest by viewing images of multiple modalities. Such a system will aid physicians in making accurate diagnoses in a more efficient manner.

It will be apparent to those skilled in the art that various modifications may be made in the present invention, without departing from the spirit or scope of the invention. Thus, it is intended that the present invention cover modifications and variations of this invention provided they come within the scope of the appended claims and their equivalents.

It is also noted that the claims may include reference signs/ numerals in accordance with PCT Rule 6.2(b). However, the present claims should not be considered to be limited to the exemplary embodiments corresponding to the reference signs/numerals.

What is claimed is:

1. A system comprising:
    an image loader including a processor processing multiple modality images, the multiple modality images including a mammogram image, an ultrasound image and an MRI image, the processing including generating diagnostic information from at least one of the multiple modality images based on a computer aided diagnostic tool; and
    an image viewer simultaneously displaying the multiple modality images and a report including both patient information and diagnostic information,
    wherein the report is displayed on a portion of the image viewer that is separate from the display of the multiple modality images.

2. The system of claim 1, wherein the processor identifies a region of interest on the multiple modality images, the diagnostic information being for the region of interest.

3. The system of claim 1, wherein the computer aided diagnostic tool includes one of an image subtraction functionality and an image segmentation functionality.

4. The system of claim 2, wherein the diagnostic information includes whether the region of interest is benign or malignant.

5. The system of claim 1, wherein the image loader further includes a memory storing the multiple modality images.

6. The system of claim 1, wherein the image viewer displays a toolbar, the toolbar including means for selecting the computer aided diagnostic tool to be executed on the multiple modality images.

7. The system of claim wherein the image viewer displays the images in a predetermined location based on the image modality.

8. The system of claim 1, wherein the multiple modality images further include an ultrasound image and a non-mammogram X-ray image.

9. The system of claim 1, wherein the mammogram image includes one of a media-lateral view and a crano-caudal (CC) view.

10. The system of claim 1, wherein the computer aided diagnostic tool includes a database comprising previously diagnosed cases.

11. A method comprising:
    loading multiple modality images, the multiple modality mages including a mammogram image, an ultrasound image and an MRI image;
    processing the multiple modality images to prepare the multiple images to be displayed, the processing including generating diagnostic information from at least one of the multiple modality images based on a computer aided diagnostic tool; and
    simultaneously displaying the multiple modality images and a report including both patient information and diagnostic information on an image viewer,
    wherein the report is displayed on a portion of the image viewer that is separate from the display of the multiple modality images.

12. The method of claim 11, wherein the diagnostic information includes a diagnosis of breast cancer and the computer aided diagnostic tool includes previously diagnosed images of breast cancer.

13. The method of claim 11, further comprising:
    analyzing the multiple modality images to identify a region of interest, the region of interest being identified by one of a user and the computer aided diagnostic tool.

14. The method of claim 11, further comprising:
    displaying a plurality of computer aided diagnostic tools; and
    receiving a selection of the computer aided diagnostic tools by a user.

15. The method of claim 11, wherein the computer aided diagnostic tool includes one of an image subtraction functionality and an image segmentation functionality.

16. The method of claim 11, wherein the multiple modality images further include a non-mammogram X-ray image.

17. A system, comprising:
- a means for receiving multiple modality images including a mammogram image, an ultrasound image and an MRI image;
- a means for processing multiple modality images, the processing including generating diagnostic information from at least one of the multiple modality images based on a computer aided diagnostic tool; and
- a means for simultaneously displaying the multiple modality images and a report including both patient information and the diagnostic information on an image viewer,
- wherein the report is displayed on a portion of the image viewer that is separate from the display of the multiple modality images.

* * * * *